US010952852B2

(12) United States Patent
Barbarino et al.

(10) Patent No.: US 10,952,852 B2
(45) Date of Patent: Mar. 23, 2021

(54) DOUBLE BASKET ASSEMBLY FOR VALVE REPAIR

(71) Applicant: Abbott Cardiovascular Systems Inc., Santa Clara, CA (US)

(72) Inventors: Casey M. Barbarino, San Francisco, CA (US); Benjamin L. Lee, Santa Clara, CA (US); Chad Abunassar, San Francisco, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 580 days.

(21) Appl. No.: 15/441,823

(22) Filed: Feb. 24, 2017

(65) Prior Publication Data

US 2018/0243086 A1 Aug. 30, 2018

(51) Int. Cl.
*A61F 2/24* (2006.01)
*A61B 17/128* (2006.01)
(Continued)

(52) U.S. Cl.
CPC ............ *A61F 2/246* (2013.01); *A61B 17/122* (2013.01); *A61B 17/128* (2013.01); *A61F 2/2463* (2013.01); *A61F 2/2466* (2013.01); *A61B 2017/00243* (2013.01); *A61B 2090/037* (2016.02); *A61F 2230/0019* (2013.01);
(Continued)

(58) Field of Classification Search
CPC ................ A61B 17/122; A61B 17/128; A61B 2017/0043; A61F 2/2454; A61F 2/2457; A61F 2/246; A61F 2/2463; A61F 2/2466; A61F 2/2469; A61F 2/2493
See application file for complete search history.

(56) References Cited

U.S. PATENT DOCUMENTS 5,171,259 A 12/1992 Inoue
5,607,445 A * 3/1997 Summers .................. A61F 2/88
606/198

(Continued)

FOREIGN PATENT DOCUMENTS

WO WO 91/15155 A1 10/1991
WO WO 2004/069055 A2 8/2004
(Continued)

OTHER PUBLICATIONS

International Search Report dated Jun. 12, 2018.
(Continued)

*Primary Examiner* — Wade Miles
*Assistant Examiner* — Kankindi Rwego
(74) *Attorney, Agent, or Firm* — Baker Botts L.L.P.

(57) ABSTRACT

The invention provides medical devices, systems and methods for tissue approximation and repair and in particular to reduce mitral regurgitation by means of improved coaptation. The devices, systems and methods of the invention will find use in a variety of therapeutic procedures, including endovascular, minimally-invasive, and open surgical procedures, and can be used in various anatomical regions, including the cardiovascular system, heart, other organs, vessels, and tissues. The invention is particularly useful in those procedures requiring minimally-invasive or endovascular access to remote tissue locations, where the instruments utilized must negotiate long, narrow, and tortuous pathways to the treatment site.

33 Claims, 14 Drawing Sheets

(51) Int. Cl.
*A61B 17/122* (2006.01)
*A61B 90/00* (2016.01)
*A61B 17/00* (2006.01)

(52) U.S. Cl.
CPC ............... *A61F 2230/0093* (2013.01); *A61F 2250/0039* (2013.01)

(56) References Cited

U.S. PATENT DOCUMENTS

| | | | |
|---|---|---|---|
| 5,924,424 | A | 7/1999 | Stevens et al. |
| 6,129,758 | A | 10/2000 | Love |
| 7,112,207 | B2 | 9/2006 | Allen et al. |
| 7,563,267 | B2 | 7/2009 | Goldfarb et al. |
| 7,563,273 | B2 | 7/2009 | Goldfarb et al. |
| 7,569,062 | B1 | 8/2009 | Kuehn et al. |
| 7,666,204 | B2 | 2/2010 | Thornton et al. |
| 8,470,028 | B2 | 6/2013 | Thornton et al. |
| 8,753,362 | B2 | 6/2014 | Widomski et al. |
| 9,180,005 | B1 | 11/2015 | Lashinski et al. |
| 9,750,505 | B2 | 9/2017 | Miles et al. |
| 9,770,232 | B2 | 9/2017 | Amin et al. |
| 2002/0013571 | A1 | 1/2002 | Goldfarb et al. |
| 2003/0018358 | A1 | 1/2003 | Saadat |
| 2003/0139819 | A1 | 7/2003 | Beer et al. |
| 2004/0073242 | A1 | 4/2004 | Chanduszko |
| 2004/0176799 | A1 | 9/2004 | Chanduszko et al. |
| 2004/0220610 | A1* | 11/2004 | Kreidler ............ A61B 17/0057 606/200 |
| 2005/0043759 | A1 | 2/2005 | Chanduszko |
| 2005/0065548 | A1 | 3/2005 | Marino et al. |
| 2005/0273135 | A1 | 12/2005 | Chanduszko et al. |
| 2005/0288786 | A1 | 12/2005 | Chanduszko |
| 2006/0122646 | A1 | 6/2006 | Corcoran et al. |
| 2006/0265004 | A1 | 11/2006 | Callaghan et al. |
| 2006/0271089 | A1 | 11/2006 | Alejandro et al. |
| 2007/0010851 | A1 | 1/2007 | Chanduszko |
| 2007/0027533 | A1 | 2/2007 | Douk |
| 2007/0073337 | A1 | 3/2007 | Abbott et al. |
| 2007/0112380 | A1 | 5/2007 | Figulla et al. |
| 2007/0167981 | A1 | 7/2007 | Opolski et al. |
| 2007/0179527 | A1 | 8/2007 | Eskuri et al. |
| 2007/0250081 | A1 | 10/2007 | Cahill et al. |
| 2007/0260305 | A1 | 11/2007 | Drews et al. |
| 2009/0188964 | A1 | 7/2009 | Orlov |
| 2010/0004740 | A1 | 1/2010 | Seguin et al. |
| 2010/0234878 | A1 | 9/2010 | Hruska et al. |
| 2010/0234885 | A1 | 9/2010 | Frazier et al. |
| 2011/0060407 | A1 | 3/2011 | Ketai et al. |
| 2011/0276086 | A1 | 11/2011 | Al-Qbandi et al. |
| 2011/0307055 | A1* | 12/2011 | Goldfarb ............ A61B 17/0469 623/2.11 |
| 2013/0066341 | A1 | 3/2013 | Ketai et al. |
| 2013/0282110 | A1 | 10/2013 | Schweich, Jr. et al. |
| 2013/0289718 | A1 | 10/2013 | Tsukashima et al. |
| 2014/0005778 | A1 | 1/2014 | Buchbinder et al. |
| 2014/0163669 | A1 | 6/2014 | Ben-zvi et al. |
| 2014/0200662 | A1 | 7/2014 | Eftel et al. |
| 2015/0066077 | A1 | 3/2015 | Akpinar |
| 2015/0173765 | A1 | 6/2015 | Miller et al. |
| 2016/0022417 | A1 | 1/2016 | Karapetian et al. |
| 2016/0030169 | A1 | 2/2016 | Shahriari |
| 2018/0055633 | A1 | 3/2018 | Costello et al. |
| 2018/0133010 | A1* | 5/2018 | Kizuka ............... A61F 2/2466 |

FOREIGN PATENT DOCUMENTS

| | | |
|---|---|---|
| WO | WO 2004/069055 A3 | 8/2004 |
| WO | WO 2014/018907 A1 | 1/2014 |
| WO | WO 2014/182849 A1 | 11/2014 |

OTHER PUBLICATIONS

International Search Report dated Jan. 29, 2018 in International Application No. PCT/US2017/062734, European Patent Office, pp. 1-4.

International Search Report dated Oct. 13, 2017 from International Application No. PCT/US2017/039811, European Patent Office ISA/EP.

Vismara et al., "Transcatheter Edge-to-Edge Treatment of Functional Tricuspid Regurgitation in an Ex Vivo Pulsatile Heart Model," JACC 68(10):1024-1033 (2016).

\* cited by examiner

DOUBLE BASKET ASSEMBLY FOR VALVE REPAIR

BACKGROUND

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different medical defects in the mitral valve or the left ventricular wall. The valve leaflets, the valve chordae that connect the leaflets to the papillary muscles, and/or the papillary muscles or the left ventricular wall may be damaged or otherwise dysfunctional. Commonly, the valve annulus may be damaged, dilated, or weakened, limiting the ability of the mitral valve to close adequately against the high pressures of the left ventricle during ventricular contraction (systole).

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

Consequently, alternative and additional methods, devices, and systems for performing the repair of mitral and other cardiac valves have been developed. Such methods, devices, and systems preferably do not require open chest access and are capable of being performed either endovascularly, i.e., using devices which are advanced to the heart from a point in the patient's vasculature remote from the heart or by a minimally invasive approach.

In some instances, however, a variety of challenges are faced in desirably fixating the valve leaflets. For example, it is commonly found in cases of mitral valve regurgitation that a portion of the leaflet is moving out of phase with the other leaflets or portions of the leaflets. This can occur due to an elongation or disconnection of the structures (chordae tendinae) holding the leaflets stable and in synchrony. Such a malfunction can lead to one leaflet or portion of a leaflet to swing or "flail" above the level of healthy coaptation, thereby allowing blood to regurgitate into the right atrium. Such flailing provides a challenge to the practitioner when attempting to fix the leaflets together, particularly via an endoscopic approach. The leaflets may be difficult to grasp, and even when grasped, the leaflets may not be desirably grasped. For example, a leaflet may only be partially grasped rather than having full contact with a grasping element. This may lead to less desirable coaptation and/or eventual slippage of the leaflet from fixation.

The foregoing remarks concerning problems and failures encountered in the mitral valve in the human heart may be made with equal validity concerning the tricuspid valve. This valve has three leaflets rather than two. The three leaflets all meet at a single point near the center of the valve and they demonstrate similar problems of malfunctioning to those shown by the mitral valve.

Therefore, devices, systems and methods are desired which stabilize the tissue, to resist flailing and other movement, prior to and/or during grasping of the tissue. Further, devices, systems and methods are desired which assist in grasping the tissue, enable more desirable coaptation of tissues, provide grasping assessment, and enable the practitioner to determine if desirable grasping of the tissues has occurred, particularly prior to fixation. Further, devices, systems and methods are desired which enable fixation assessment, enabling the practitioner to determine if desirable fixation of the tissues has occurred. These would be useful for repair of tissues in the body other than leaflets and other than heart valves. At least some of these objectives will be met by the embodiments described herein below.

SUMMARY OF THE INVENTION

The present invention provides a variety of devices, systems and methods for stabilizing, grasping, assessing and fixating tissues, particularly valve leaflets in the treatment of cardiac valve regurgitation, more particularly mitral valve regurgitation. Many of the devices, systems and methods utilize or are utilized in conjunction with a preferred embodiment of a fixation device having at least one distal element and at least one proximal element, wherein the tissue is grasped therebetween. When treating valve leaflets, the leaflets are typically grasped to position the fixation device at a location along the line of coaptation at a location that reduces regurgitation of the valve, such as near the center of the valve simulating a standard surgical bow-tie repair. More than one fixation device may be placed, however, and in various arrangements, as will be discussed in later sections. As used herein, the term proximal shall refer to the direction closer to the user of the device, out-of-body. The term distal shall refer to the direction further into the body of the patient and away from the user.

In a further aspect, the invention provides an interventional system comprising a tubular guide having a proximal end, a proximal end and a lumen therebetween, the proximal end of the tubular guide being deflectable about a first axis; a delivery catheter positionable through the lumen, the delivery catheter having a flexible shaft with a proximal end, a distal end, a lumen therebetween, and an actuation element movably disposed in the lumen; and a fixation device having a coupling member releasably coupled to the proximal end of the shaft, a first proximal member movably coupled to the coupling member, and a first distal member, the first proximal element being releasably coupled to the actuation element and movable therewith, the first proximal element and the first distal element being adapted to engage tissue therebetween.

In one embodiment a medical device for repairing valve tissue includes a proximal member having a tapered shape in an expanded configuration and a tubular shape in a compressed configuration and a distal member having a tapered shape in an expanded configuration and a tubular shape in a compressed configuration. An elongated shaft extends through the proximal member and the distal member to connect the proximal member to the distal member. The distal member is fixed to the elongated shaft and the proximal member is configured for slidable axial movement along the elongated shaft. A locking member is used to lock the proximal member to the distal member after the proximal member is moved into contact with distal member with the valve tissue positioned therebetween. The proximal member and the distal member are formed from a lattice structure having rigidity in the expanded configuration, and longitudinal flexibility in the compressed configuration. In this embodiment, the proximal member and the distal member are self-expanding from the compressed configuration to the expanded configuration and are formed from a self-expanding shape memory material including NITINOL®, ELGILOY®, or a self-expanding polymer. The locking member includes a ball mounted to a distal end of the elongated shaft and having a diameter that is greater than a diameter of a proximal portion of the proximal member so that as the elongated shaft is moved proximally, the ball pulls a proximal end of the distal member into the distal portion of the proximal member thereby locking the proximal member to the distal member with the valve tissue therebetween.

In another embodiment, a medical device for repairing valve tissue includes a proximal basket having a tapered shape in an expanded configuration and a tubular shape in a compressed configuration and a distal basket having a tapered shape in an expanded configuration and a tubular shape in a compressed configuration. An elongated shaft extends through the proximal basket and the distal basket to connect the proximal basket to the distal basket. The distal basket being fixed to the elongated shaft and the proximal basket being configured for slidable axial movement along the elongated shaft; and a locking ball to lock the proximal basket to the distal basket after the proximal basket is moved into contact with distal basket with the valve tissue positioned therebetween. The proximal basket and the distal basket are formed from a lattice structure having rigidity in the expanded configuration, and longitudinal flexibility in the compressed configuration. The proximal basket and the distal basket are self-expanding from the compressed configuration to the expanded configuration. The locking member includes a ball mounted to a distal end of the elongated shaft and having a diameter that is greater than a diameter of a distal portion of the proximal basket so that as the elongated shaft is moved proximally, the ball pulls a proximal end of the distal basket into the proximal portion of the proximal basket thereby locking the proximal basket to the distal basket with the valve tissue therebetween.

The delivery device of the invention is adapted to allow the user to deliver the fixation device to the target site from a remote access point, whether through endovascular or surgical approaches, align the device with the target tissue, and to selectively lock or unlock the proximal element. In some embodiments, the delivery device will have a highly flexible, kink resistant, torsionally stiff shaft with minimal elongation and high compressive strength. The delivery device will also have the movable components and associated actuators to move the distal member and the proximal member between the open and closed positions, to move the distal member into engagement with the target tissue, to lock the locking mechanism, and to detach the proximal member and the distal member from the delivery catheter. In a preferred embodiment, the delivery device comprises a delivery catheter having an elongated shaft which has an inner lumen. The proximal end of the shaft is configured for detachable connection to the coupling member of the fixation device. An actuator rod is slidably disposed in the inner lumen and is adapted for detachable coupling to the ball or other component of the fixation device that moves the proximal member. Lines for actuating the distal member and the unlocking mechanism of the fixation device extend through these tubular guides and are detachably coupled to the distal member and unlocking mechanisms.

BRIEF DESCRIPTION OF THE DRAWINGS

FIGS. 4C-4E are alternative transverse cross-sectional views taken along the lines 4C-4E through 4C-4E depicting alternative cross-sectional shapes that the struts may assume in making up the lattice structure of the valve repair assembly.

DETAILED DESCRIPTION OF THE PREFERRED EMBODIMENTS

Figure 1:
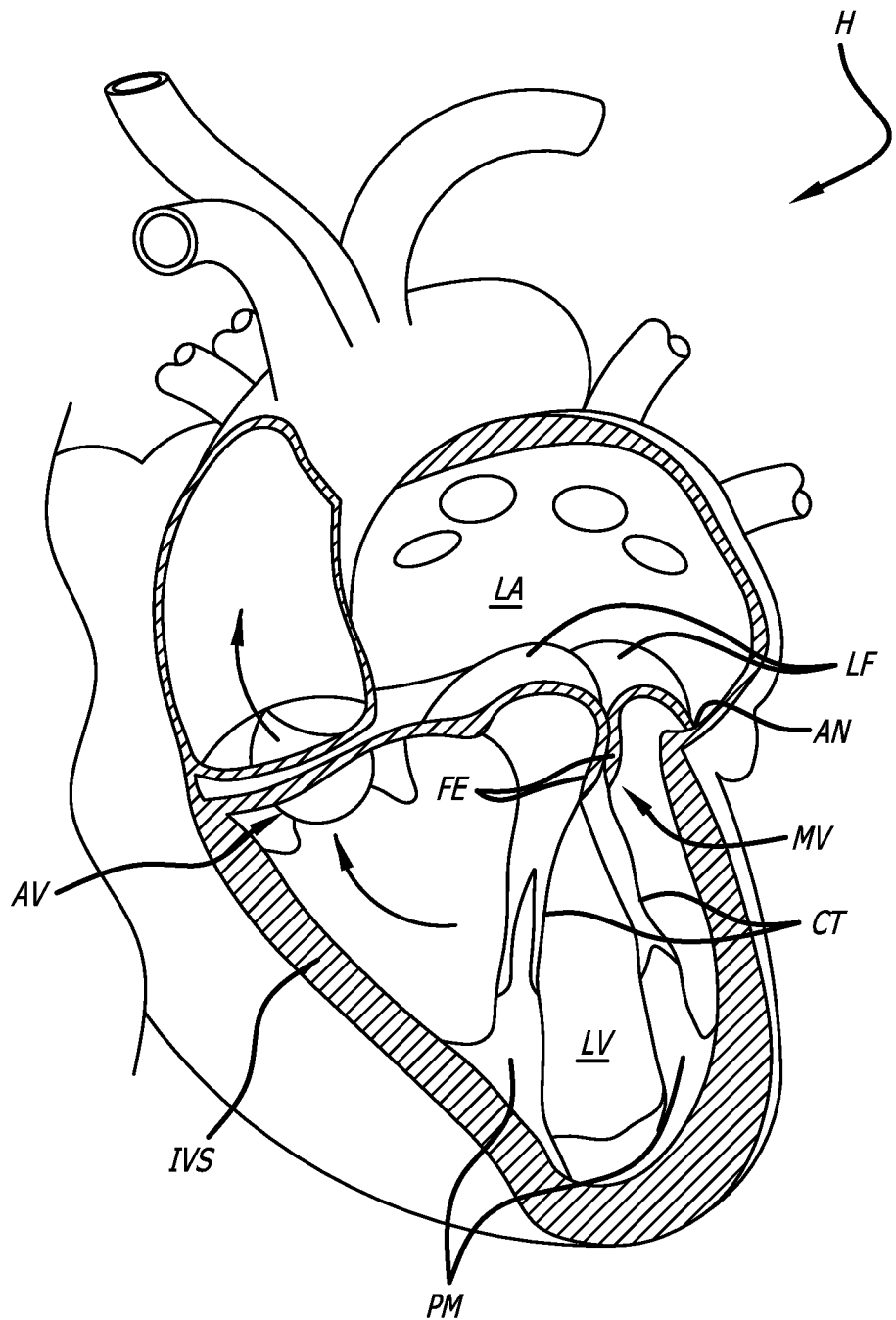
FIG. 1 depicts the left ventricle and left atrium of the heart during systole.

The left ventricle LV of a normal heart H in systole is illustrated in FIG. 1. The left ventricle LV is contracting and blood flows outwardly through the aortic valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figure 2A:
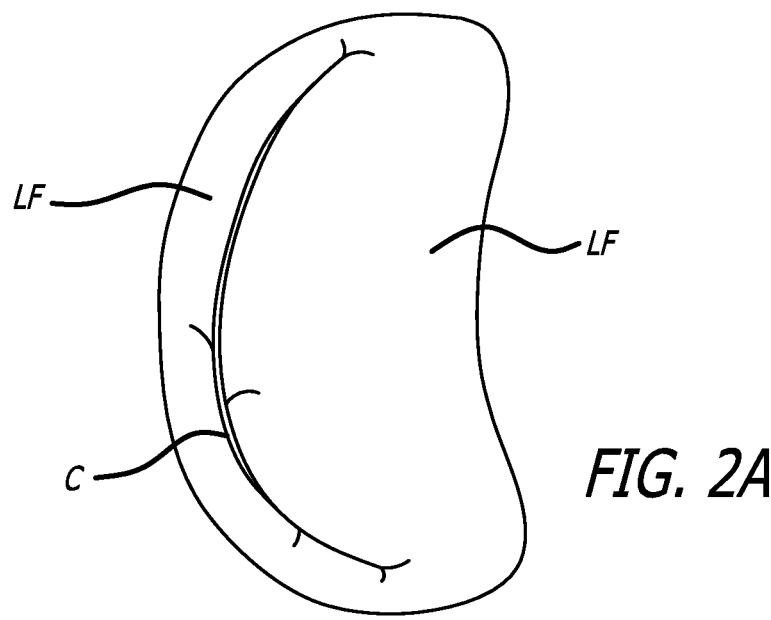
FIG. 2A depicts free edges of leaflets in normal coaptation.
Figure 2B:
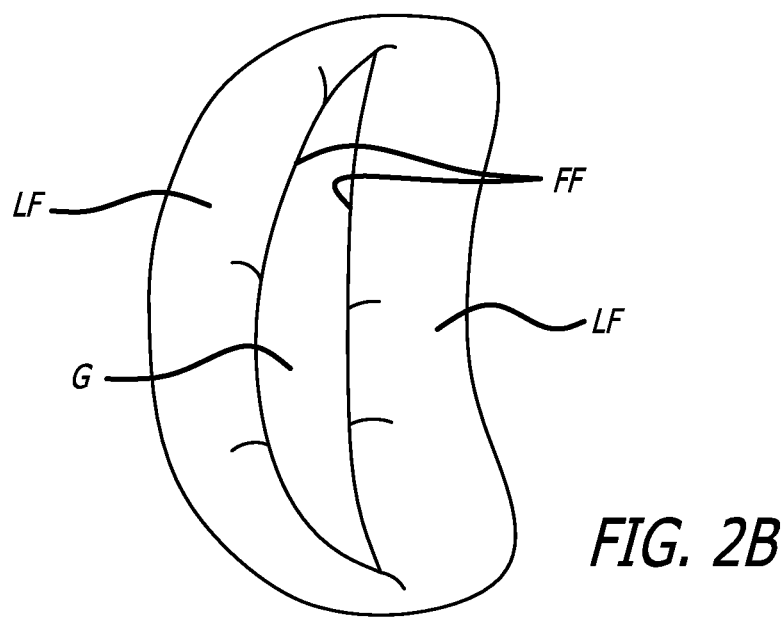
FIG. 2B illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation C. An example of a defect causing regurgitation is shown in FIG. 2B. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. In this case, while the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper valve closure. The foregoing remarks concerning problems and failures encountered in the mitral valve in the human heart may be made with equal validity concerning the tricuspid valve. This valve has three leaflets rather than two, The three leaflets all meet at a single point near the center of the valve and they demonstrate similar problems of malfunctioning to those shown by the mitral valve.

The present invention provides devices, systems and methods for stabilizing and grasping tissues such as valve leaflets, assessing the grasp of these tissues, approximating and fixating the tissues, and assessing the fixation of the tissues to treat cardiac valve regurgitation, particularly mitral valve regurgitation or tricuspid regurgitation.

Grasping will preferably be atraumatic providing a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic." In addition, it will be understood that in some cases it may be necessary or desirable to pierce or otherwise permanently affect the leaflets during either grasping, fixing or both. In addition, once a leaflet is grasped, it may be desirable to further incorporate leaflet tissue to ensure that the initial grasp will result in secure tissue fixation. Furthermore, it may be desirable once the leaflet is grasped to provide the user with feedback that sufficient leaflet is incorporated, and/or to provide the user an indication of the resulting placement, both prior to releasing the fixation device thereby allowing repositioning or correction of the placement if desired.

It may be appreciated that each step of stabilizing, grasping, approximating, fixating and assessing may be accomplished by a separate device or a plurality of steps may be accomplished by a single device. In some embodiments, all of the steps may be achieved by a single device. Further, in some embodiments, steps are provided by separate devices which approach the tissue from different directions. For example, when treating a mitral valve, some devices may use an atrial approach while other devices use a ventricular approach. Although a number of embodiments are provided to achieve these results, a general overview of the basic features will be presented herein. Such features are not intended to limit the scope of the invention and are presented with the aim of providing a basis for descriptions of individual embodiments presented later in the application.

In keeping with the invention, and referring to FIGS. 3-6C, a valve repair assembly 10 is configured in the form of a pair of basket shaped members in order to repair a mitral valve, or similar body organ. Broadly defined, a "basket" shape is one having a concave surface on one side and, on a reverse side, a convex surface. The result is a shape having an overall conical taper towards a center point on both surfaces.

In this embodiment, a distal member 12 and a proximal member 14 are attached to each other by elongated shaft 16. As used herein, the distal member 12 and proximal member 14 can be referred to as a first basket and a second basket respectively. A locking member 18 is associated with the distal member 12. The locking member 18 includes a ball 20 that resides at a proximal end 24 of the distal member 12. The ball 20 is attached to the elongated shaft and has a ball diameter 22 in the range of 0.0787 in. to 0.5512 in. (2 mm to 14 mm). In this embodiment, the proximal end 24 and a distal end 26 define a length 27 of the distal member 12. The length 27 of the distal member can vary depending upon the body organ in which it is used. In one embodiment, for use in mitral valve repair, the distal member 12 has a length 27 in the range of 0.3937 in. to 1.5748 in. (10 mm to 40 mm). Similarly, the proximal member 14 has a proximal end 32 and a distal end 34, with a length 35 being the distance between the proximal end and the distal end. The length 35 of the proximal member 14 also can vary, and in this embodiment for treating a mitral valve, is in the range of 0.3937 in. to 1.5748 in. (10 mm to 40 mm). The distal member 12 has a first diameter 28 at the distal end 26 and a second diameter 30 at the proximal end 24. The diameters of the distal member 12 can vary depending upon the body organ in which the device is implanted. In this embodiment, the first diameter 28 of the distal end 26 is in the range of 0.1575 in. to 1.1811 in. (4 mm to 30 mm) and the second diameter 30 of the proximal end 24 is in the range of 0.0787 in. to 0.6299 in. (2 mm to 16 mm). The first diameter 28 is greater than the second diameter 30 resulting in the distal member 12 having a tapered configuration, in which the diameter reduces towards the proximal end. Similarly, the proximal member 14 has a proximal member first diameter 36 and a proximal member second diameter 38. The second diameter 38 at the proximal end 32 of the proximal member 14 is in the range of 0.0787 in. to 0.6299 in. (2 mm to 16 mm). The first diameter 36 of the proximal member 14 is greater than the second diameter 38, resulting in the proximal member 14 having a tapered configuration in which the diameter reduces towards the proximal end. Preferably, the length of the distal member 12 is less than the length of the proximal member 14 for use in repairing a mitral valve. Further, it is preferred that the first diameter 28 and second diameter 30 of the distal member 12 be smaller respectively than the first diameter 36 and the second diameter 38 of the proximal member 14. The smaller distal member 12 thereby can lock into the larger proximal member 14 with the valve tissue pressed and locked therebetween. It will be appreciated that both distal member and proximal member, defining a tapered outer shape, also define a tapered inner volume wherein the tapered inner volume reduces in diameter towards the proximal direction.

Figure 6A:
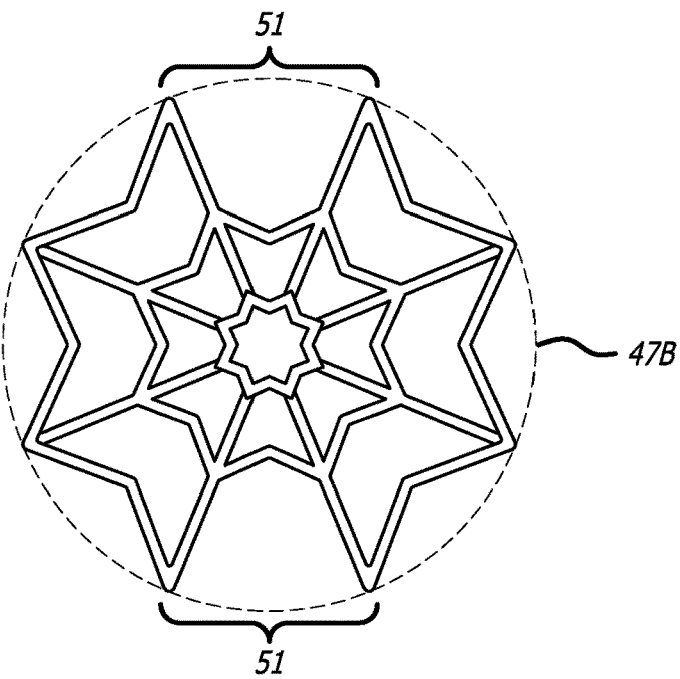
FIGS. 6A-6C are top schematic views of the proximal member or basket depicting circular, ovoid and D-shaped configurations, respectively, of the valve repair assembly.
Figure 6B:
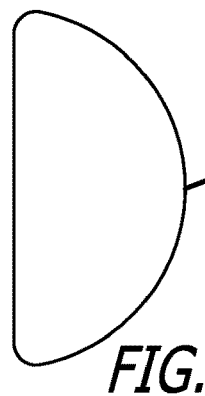
Figure 6C:
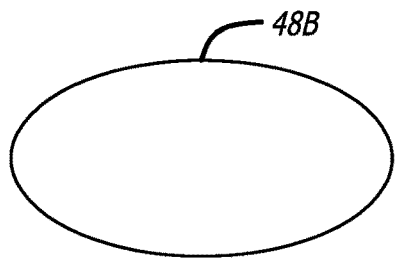

As further shown in FIGS. 3-6C, the valve repair assembly 10 is formed from a lattice structure 40 that includes struts 41 arranged so that the valve repair assembly can be compressed and expanded as necessary. Thus, the distal member 12 and the proximal member 14 are formed from a lattice structure 40 that has struts 41 that are interconnected so that the distal and proximal members can be compressed and inserted into a tubular member for delivery through the vasculature, and expanded into a tapered basket shape and locked together to repair valve tissue. As shown in FIGS. 4C-4E, the struts 41 of the lattice structure have a rectangular cross-sectional configuration 42, and in other embodiments, have a circular cross-sectional configuration 44 and an ovoid cross-sectional configuration 45. As shown in FIGS. 5A-5C, the distal member 12 has a transverse cross-sectional shape having any of the alternative forms of circular 47A, ovoid 48A, elliptical (not shown), D-shaped 49A and non-circular (not shown). Likewise, the proximal member 14, as shown in FIGS. 6A-6C, has a transverse cross-sectional shape having any of the alternative forms of circular 47B, ovoid 48B, and D-shaped 49B. In the embodiment shown in FIG. 6A and the other figures, there may be two opposing discontinuities 51 in the distal circumference of the proximal member 14. These are provided to permit opposing leaflets 66 to slide into the interior concave space of the proximal member 14, where they may be trapped between structure of the proximal member 14 and structure of the distal member 12. It will be appreciated that such a discontinuity at the distal end of the proximal member will facilitate capture of the leaflets, by allowing them to enter such concave space despite extending linearly across the distal end of the proximal member 14.

Figure 3:
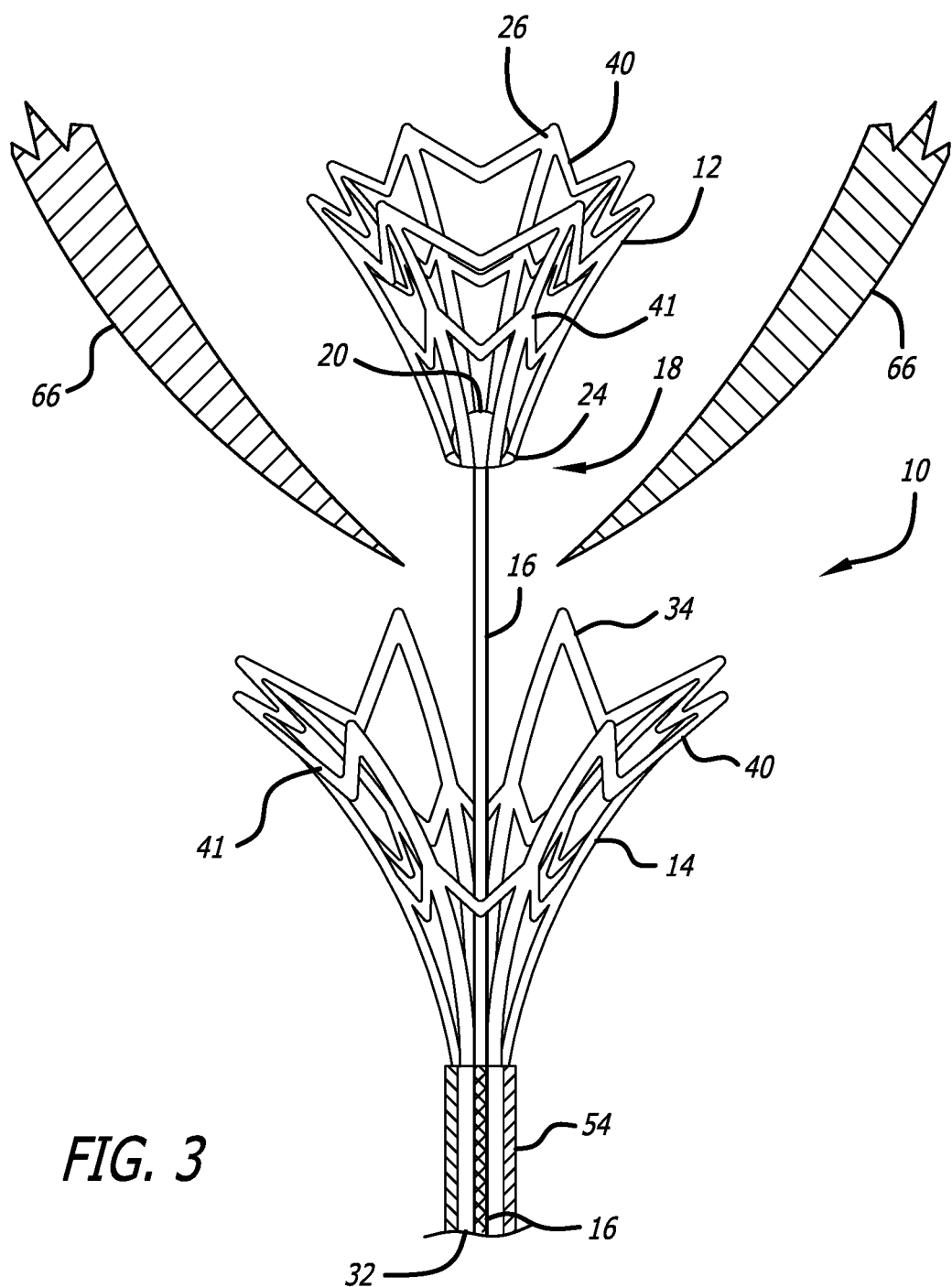
FIG. 3 is a schematic view in side perspective depicting the valve repair assembly in a deployed configuration with the mitral valve leaflets positioned therebetween.
Figure 4A:
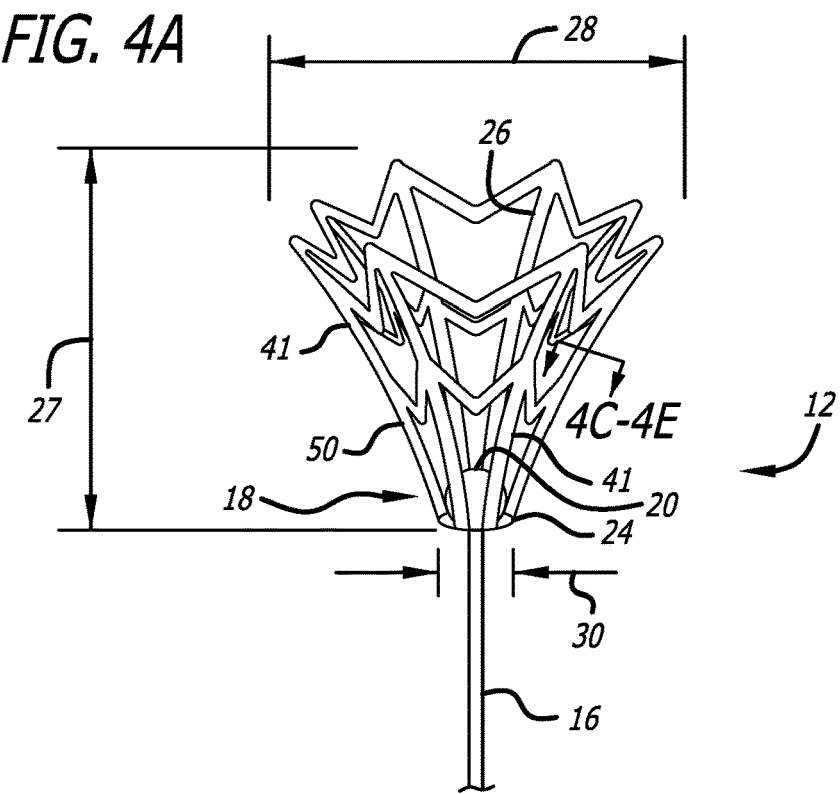
FIG. 4A is a schematic view in side perspective depicting the distal member or basket of the valve repair assembly.
Figure 4B:
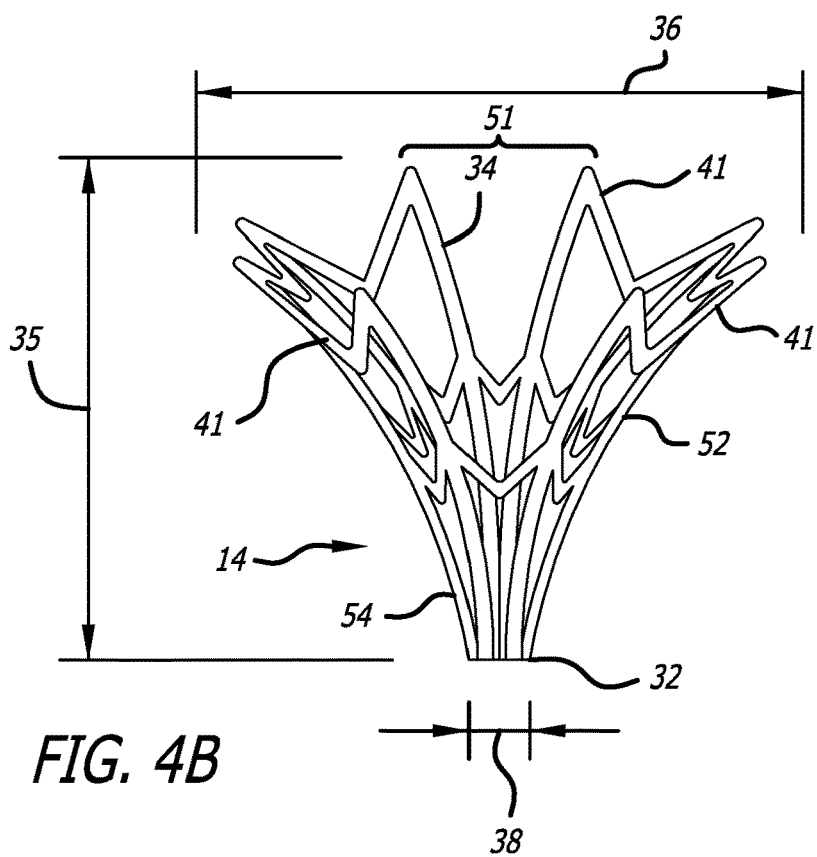
FIG. 4B is a schematic view in side perspective depicting the proximal member or basket of the valve repair assembly.
Figure 5A:
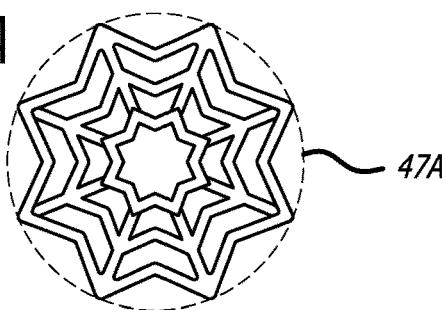
FIGS. 5A-5C are top schematic views depicting a circular, ovoid, and D-shaped configurations, respectively, of the distal member or basket of the valve repair assembly.
Figure 5B:
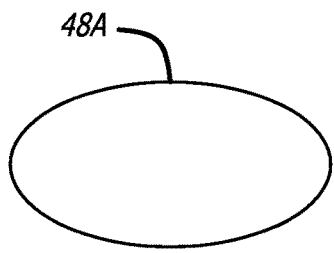
Figure 5C:
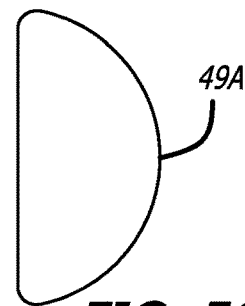

Further as shown in FIGS. 3-4B, the distal member 12 has a tapered portion 50 and the proximal member 14 has a tapered portion 52. The tapered portion 52 of the proximal member is attached to a tubular portion 54 extending proximally of the tapered portion 52. In one embodiment, the tubular portion 54 has a diameter in the range of 0.0787 in. to 0.4724 in. (2 mm to 12 mm).

Figure 7:
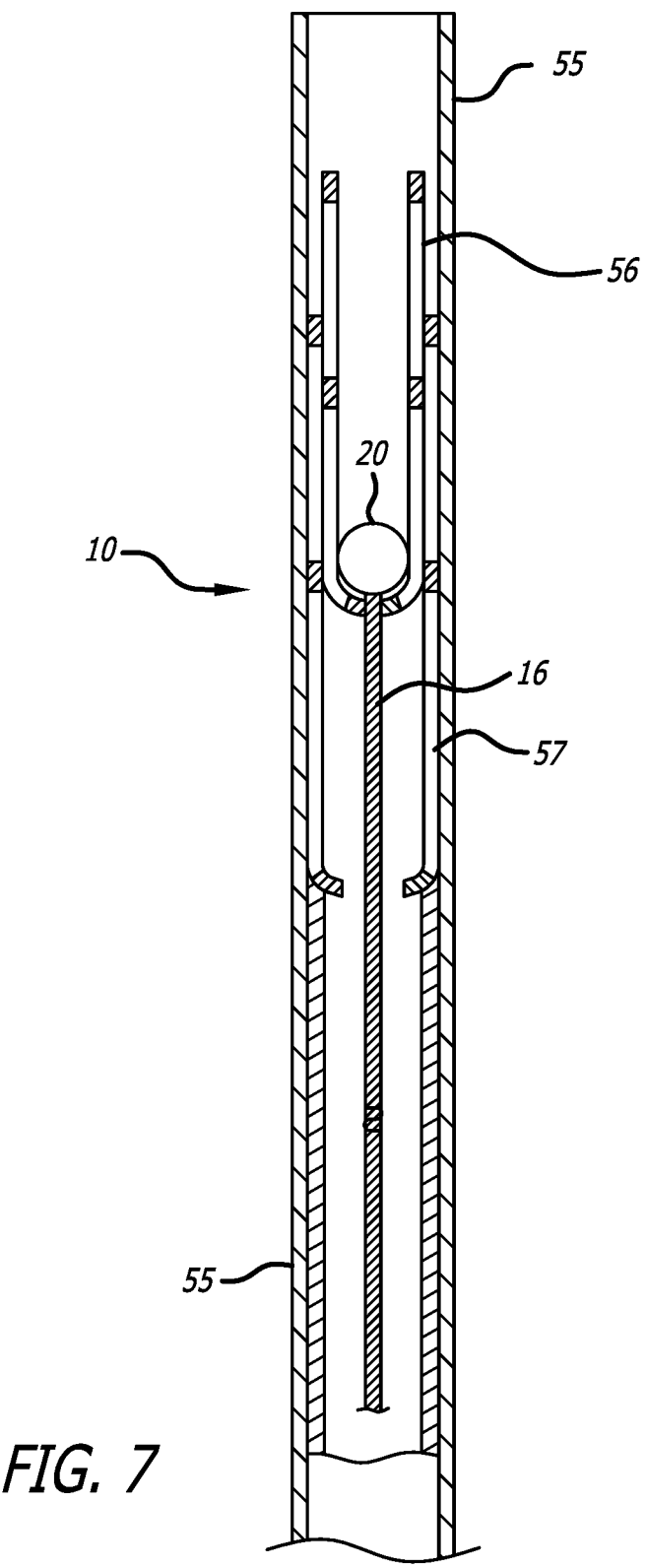
FIG. 7 is a cross-sectional view of the valve repair assembly in a compressed configuration inside a tubular member.

As shown in FIG. 7, the valve repair assembly 10 is compressed and positioned inside of tubular member 55. The valve repair assembly is axially slidable inside the tubular member. Since the compressed distal member 56 and the compressed proximal member 57 of the valve repair assembly are formed from a shape memory alloy, their lattice structure 40 is easily compressible to fit inside the tubular member 55, and each will self-expand when pushed out of the tubular member.

Figure 8:
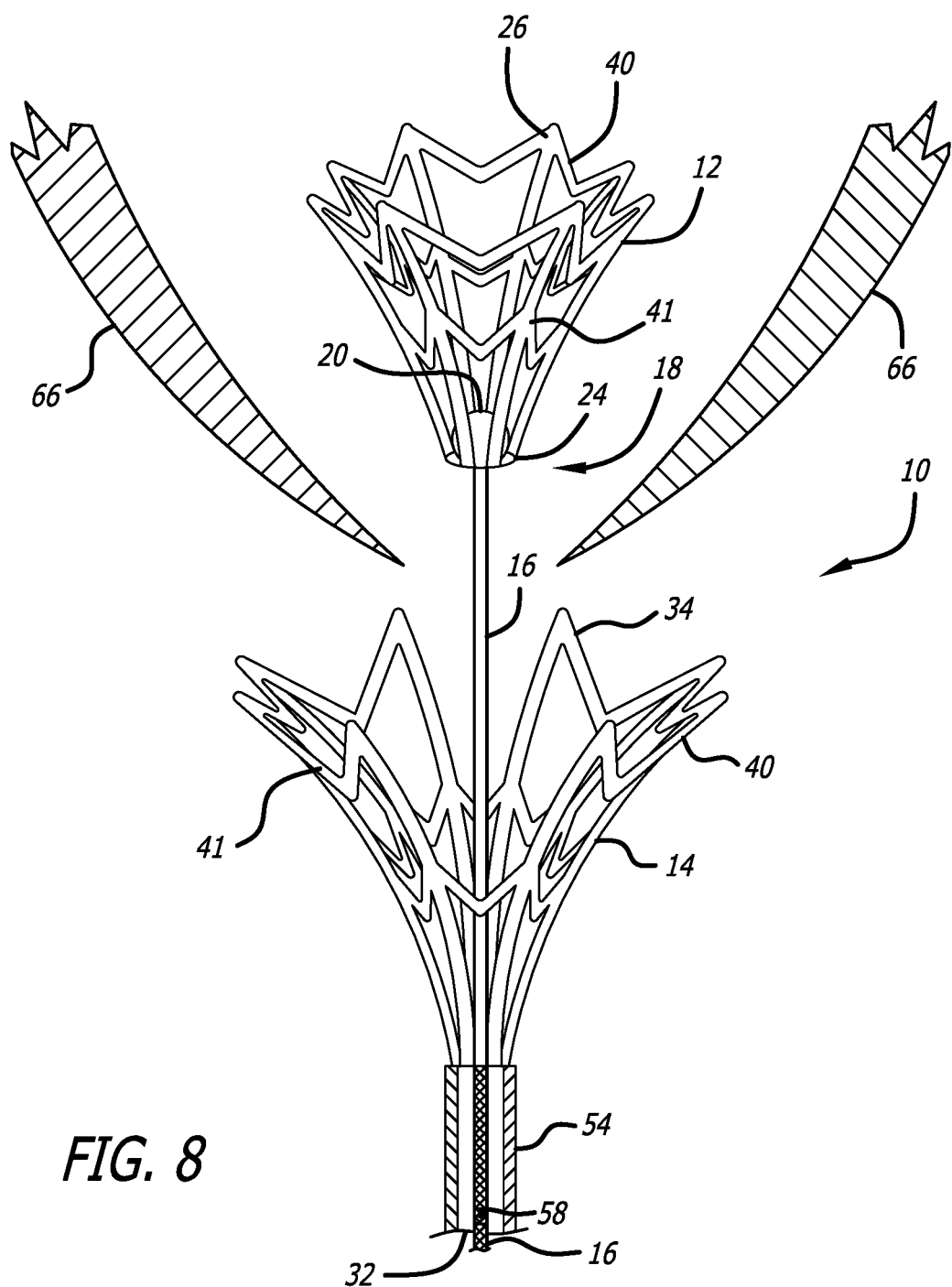
FIG. 8 is a schematic view in side perspective of the valve repair assembly, partially in section, with the valve leaflets positioned between the distal member and the proximal member. This view shows insertion of the assembly via a transapical approach, from the bottom of the left ventricle.
Figure 9:
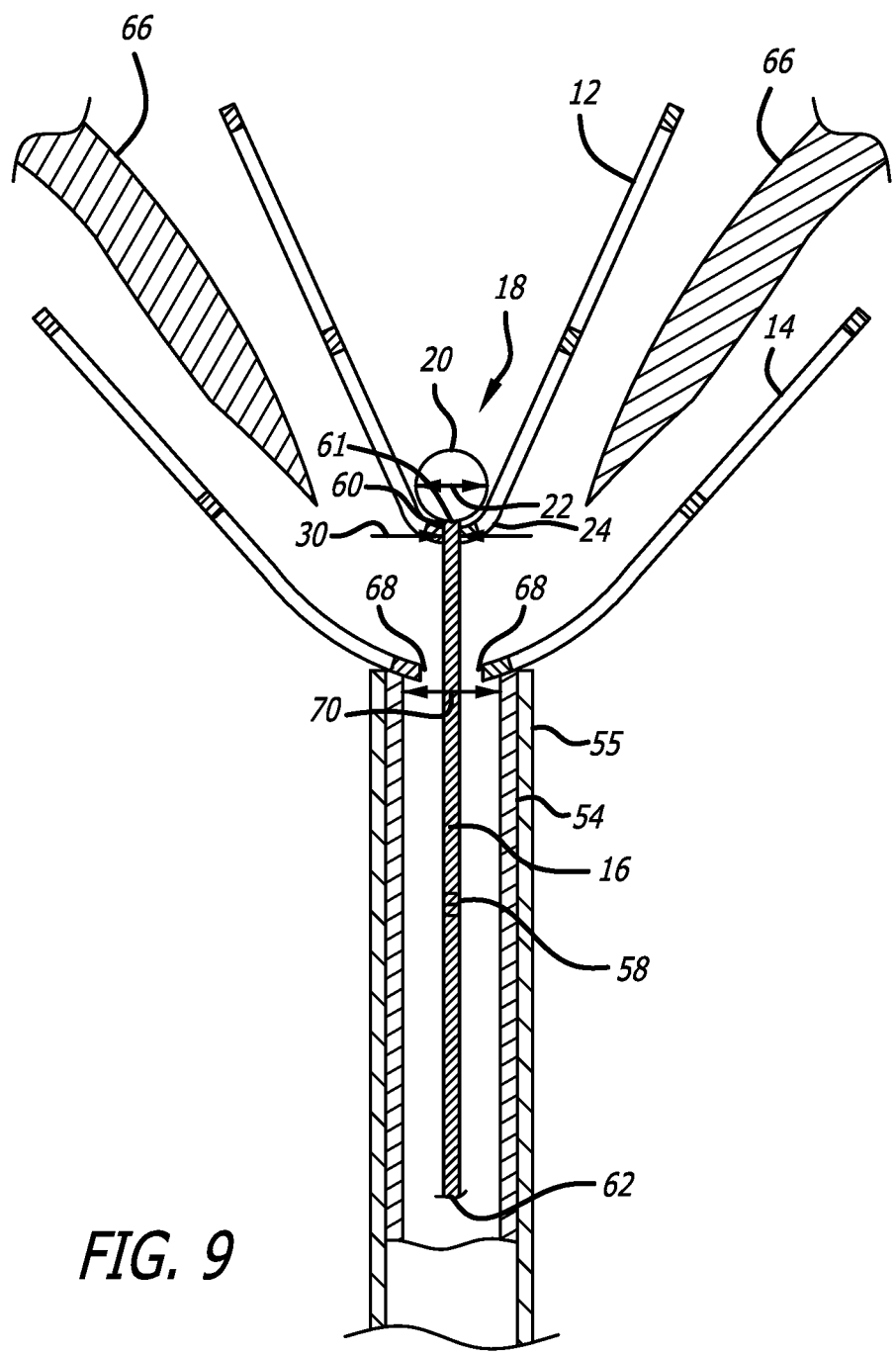
FIG. 9 is a cross-sectional side view of the valve repair assembly depicting the distal member being drawn into locking engagement with the proximal member, with the valve leaflets sandwiched therebetween. This view shows insertion of the assembly via a transapical approach, from the bottom of the left ventrical.
Figure 10:
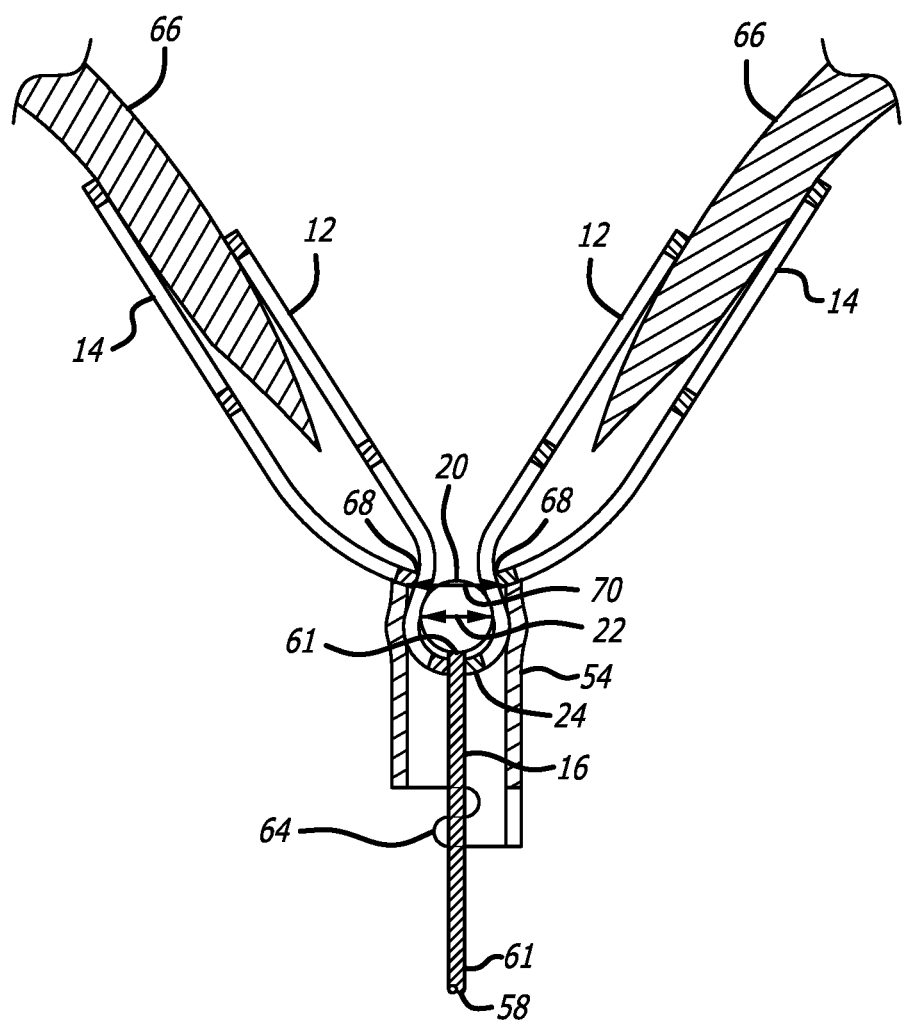
FIG. 10 is a partial side cross-sectional view of the valve repair assembly depicting the locking ball positioned in the tubular portion of the proximal member of the valve repair assembly, with the valve leaflets sandwiched between the distal member and the proximal member.

In order to implant the valve repair assembly 10 in the mitral valve, FIGS. 8, 9 and 10 depict the locking member 18 including ball 20 which is attached at attachment point 60 on the distal end 61 of the elongated shaft 16. The elongated shaft proximal end 62 extends past the proximal end 32 of proximal member 14 and S-shaped discontinuity 58 is at the proximal end 62 of the elongated shaft. A sheath (not shown) surrounds the discontinuity, and when the sheath is withdrawn from around the discontinuity 58, the shortened portion of the shaft 16 (FIG. 10) is all that remains in the body. In order to lock the proximal member 14 to the distal member 12, the proximal member 14 is positioned under the valve leaflets 66 (proximal to the valve leaflets) and the distal member 12 is pulled proximally by pulling proximally on the elongated shaft 16. The distal member 12 is attached to the elongated shaft 16 while the proximal member 14 is sized for slidable movement over the elongated shaft. The ball 20 of the locking member has a diameter 22 that is greater than the second diameter 30 at the proximal end 24 of the distal member 12 so that the ball will not pull through the proximal end of the distal member. By continuing to pull proximally on the elongated shaft, the distal member 12 is pulled into contact with the proximal member 14 thereby wedging the valve leaflets 66 therebetween. To lock the proximal member 14 to the distal member 12, the ball 20 and the proximal end 24 of the distal member are forced through opening 68 in the proximal member 14 and into the tubular portion 54 of the proximal member 14. The ball diameter 22 is slightly greater than the diameter 70 of opening 68 in the proximal member 14, thereby creating a friction fit sufficient to lock the distal member 12 and the proximal member 14 securely together, even in the high pressure blood flow environment associated with the mitral valve. (As used herein, the term friction fit shall include detent fit and mechanical engagement.) In this embodiment, the ball diameter is in the range of 0.0787 in. to 0.5512 in. (2 mm to 14 mm) and the opening diameter 70 is in the range of 0.0787 in. to 0.4724 in (2 mm to 12 mm). In one preferred embodiment, the ball 20 has a diameter of 0.1575 in. (4 mm), and the opening diameter 70 of the tubular portion is 0.1181 in. (3 mm). Since the proximal member is formed from the expandable lattice structure 40, and hence the tubular portion 54 as well, as the ball is pulled into the tubular portion, the tubular portion will stretch or expand slightly to accommodate the ball and create a locking friction fit. The ball is pulled into the tubular portion 54 of the proximal member 14, which is also smaller in diameter than the ball. With the ball 20 and proximal end 24 of the distal member 12 pulled into and wedged in the tubular portion 54, the distal member 12 and proximal member 14 are firmly attached with the mitral valve leaflets 66 sandwiched therebetween. Further, the distal member 12 preferably is smaller in overall size than the proximal member 14, so that as the two members are brought into contact as described above, the smaller distal member 12 wedges into the larger proximal member 14, thereby coapting the mitral valve leaflets therebetween.

As most clearly shown in FIG. 10, after the distal member 12 and the proximal member 14 are locked together, a sheath (not shown) that surrounds tubular portion 54 is withdrawn and discontinuity 64 operates in a known manner so that only the short portion attached to the proximal member 14 of the tubular portion 54 remains in the body while the rest of the tubular portion is withdrawn from the body in a known manner.

Figure 9A:
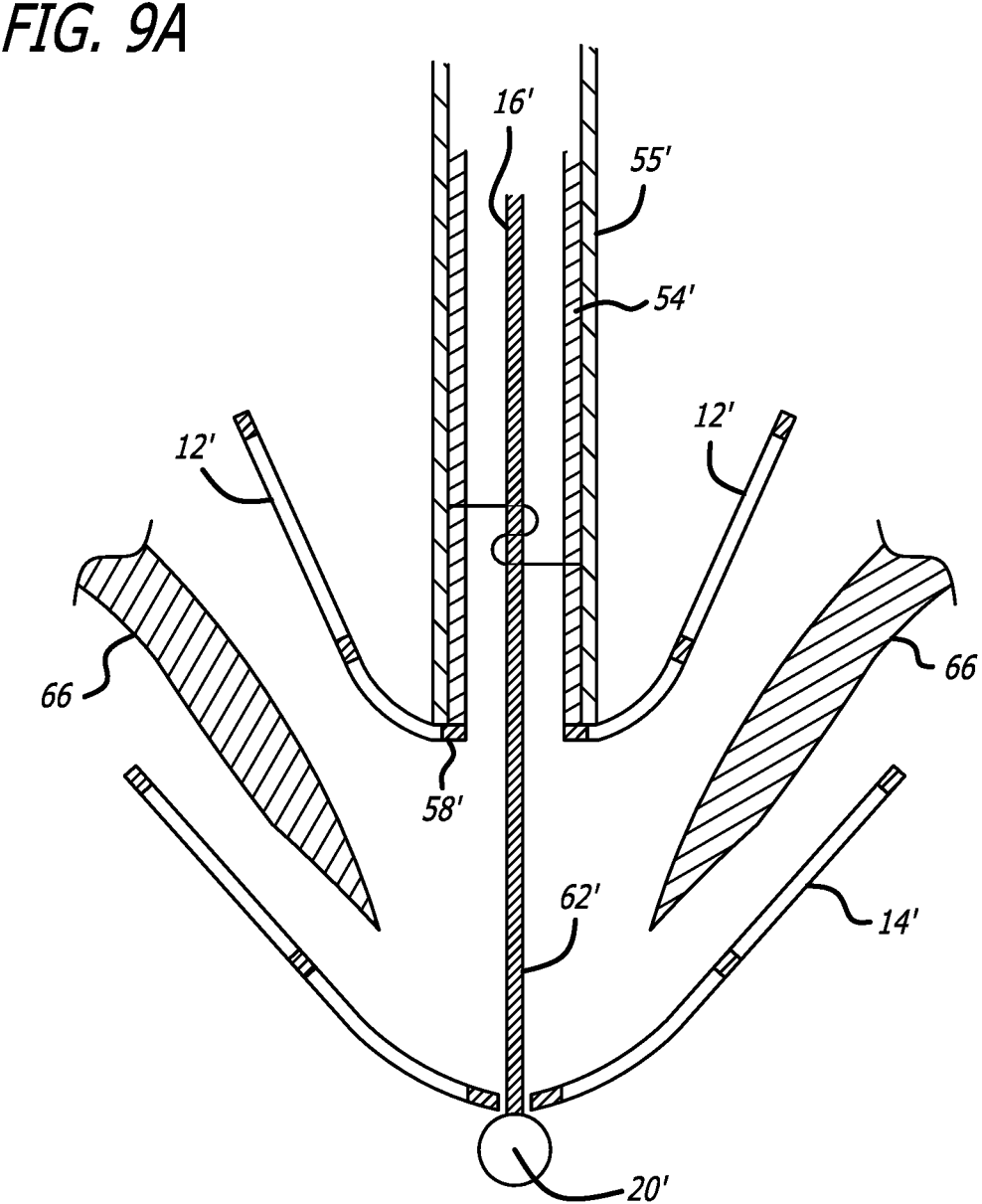
FIG. 9A is a cross-sectional side view of another embodiment of the valve repair assembly. In this embodiment, a delivery system is located on an opposite side of a repair assembly, thereby permitting insertion of the resulting assembly via a trans-septal approach from the left atrium.
Figure 10A:
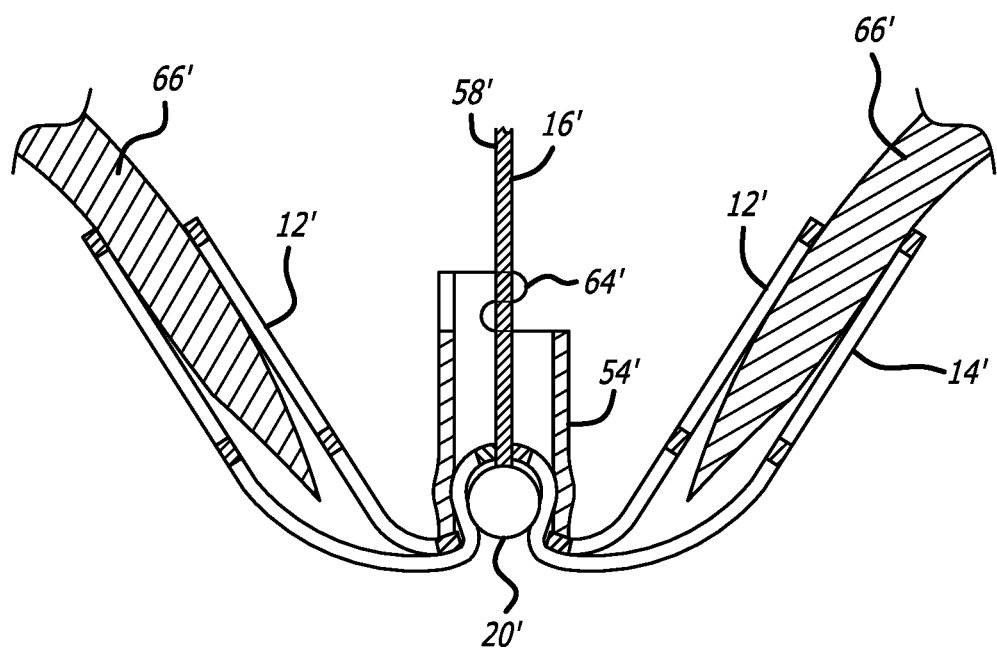
FIG. 10A is a partial side cross-sectional view of the embodiment shown in FIG. 9A, with valve leaflets sandwiched between two members that are locked together by a locking ball.

It will be evident to one of ordinary skill in the art that FIGS. 9 and 10 show an approach by the assembly towards the leaflets via a transapical approach, namely via the bottom of the left ventrical. However, FIG. 9A and FIG. 10A show an alternative embodiment in which the delivery mechanism is positioned on a reverse side of the repair mechanism from that depicted in FIG. 9 and FIG. 10. In this new embodiment, the logic of delivery is similar to the foregoing, but entry to the heart is achieved, for example, trans-septally from above the valve via the left atrium. To emphasize the alternative embodiment, each element of the previous embodiment is identified in the new embodiment by appending a "dash" to the identifying numeral. For example, the first member 12 shown in FIGS. 9 and 10 is shown as first member 12' in FIGS. 9A and 10A. One of ordinary skill in the art will follow the procedure for deploying the embodiment of FIGS. 9A and 10A from the description of the previous embodiment, when read together with FIGS. 9A and 10A.

Figure 11:
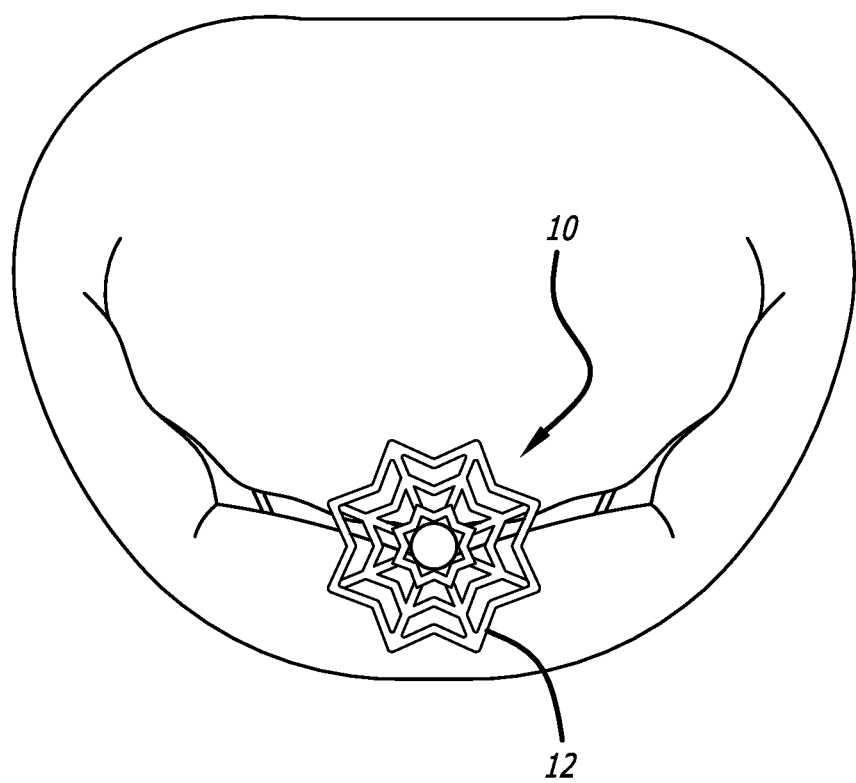
FIG. 11 is a top plan view of the mitral valve with a valve repair assembly implanted across the leaflets of the valve.

FIG. 11 depicts the valve repair assembly 10 fastened to the mitral valve leaflets and closing any unwanted opening between the leaflets. The mitral valve can function normally with the valve repair assembly attached since the valve can open and close around the assembly. Importantly, with the valve repair assembly implanted, the leaflets 66 of the mitral valve can function normally with the support of the assembly, thereby reducing the likelihood of regurgitation.

Figure 12:
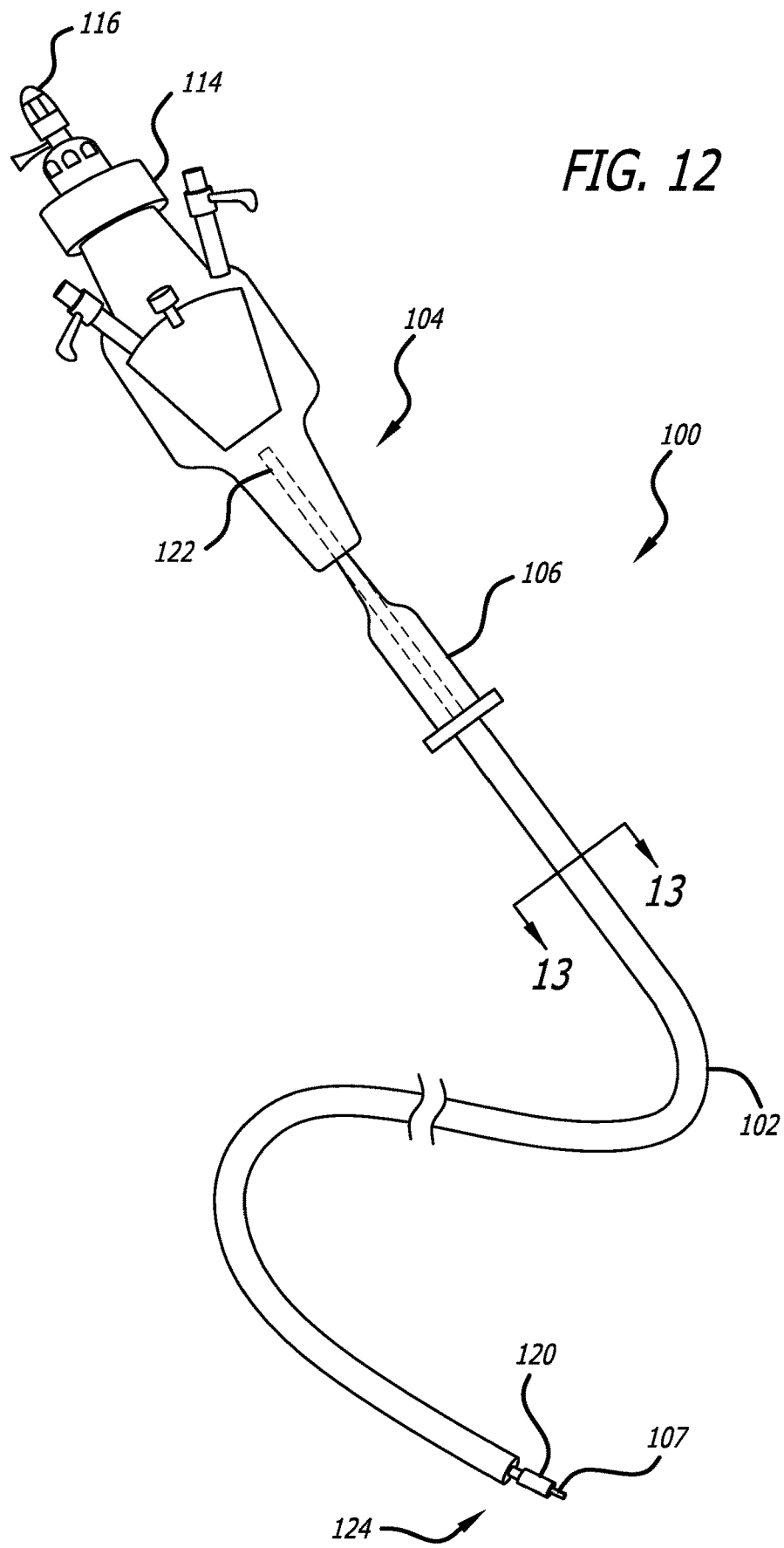
FIG. 12 is a schematic view of a delivery catheter assembly for delivering and implanting the valve repair assembly in a mitral valve.

FIG. 12 shows an embodiment of a delivery device or delivery catheter 100 which may be used to introduce and position the valve repair assembly 10 as described above. The delivery catheter 100 includes a shaft 102, having a distal end 122 and a proximal end 124, and a handle 104 attached to the distal end 122. A valve repair assembly 10 (not shown) is removably coupleable to the proximal end 124 for delivery to a site within the body, typically for endovascular delivery to the mitral valve. Thus, extending from the proximal end 124 is a coupling structure 120 for coupling with the valve repair assembly 10. Also extending from the proximal end 124 is an actuator rod 107. The actuator rod 107 is connectable with the valve repair assembly 10 and acts to manipulate the valve repair assembly 10, typically opening and deploying the distal member 12 and the proximal member 14.

Referring to FIG. 12, the handle 104 is attached to the distal end 122 of the shaft 107 and is used to manipulate the valve repair assembly 10 and to optionally decouple the valve repair assembly 10 for permanent implantation. The valve repair assembly 10 is primarily manipulated by the actuator rod 107. The actuator rod 107 manipulates the distal member 12, the proximal member 14, and the elongated shaft 16 to push the valve repair assembly 10 out of the proximal end 124 of the shaft 102. In this embodiment, the actuator rod 107 may be translated (extended or retracted) to manipulate the valve repair assembly 10. This is achieved with the use of the actuator rod control 114. The actuator rod 107 may also be rotated to better position the valve repair assembly 10 in the vasculature or in the mitral valve. This is achieved with the use of the actuator rod handle 116. The actuator rod handle 116 and actuator rod control 114 are joined with a main body 108 within which the actuator rod 107 is guided into the shaft 102. The handle 104 further includes a support base 106 connected with the main body 108. The main body 108 is slideable along the support base 106 to provide translation of the shaft 102. Further, the main body 108 is rotatable around the support base 106 to rotate the shaft.

Figure 13:
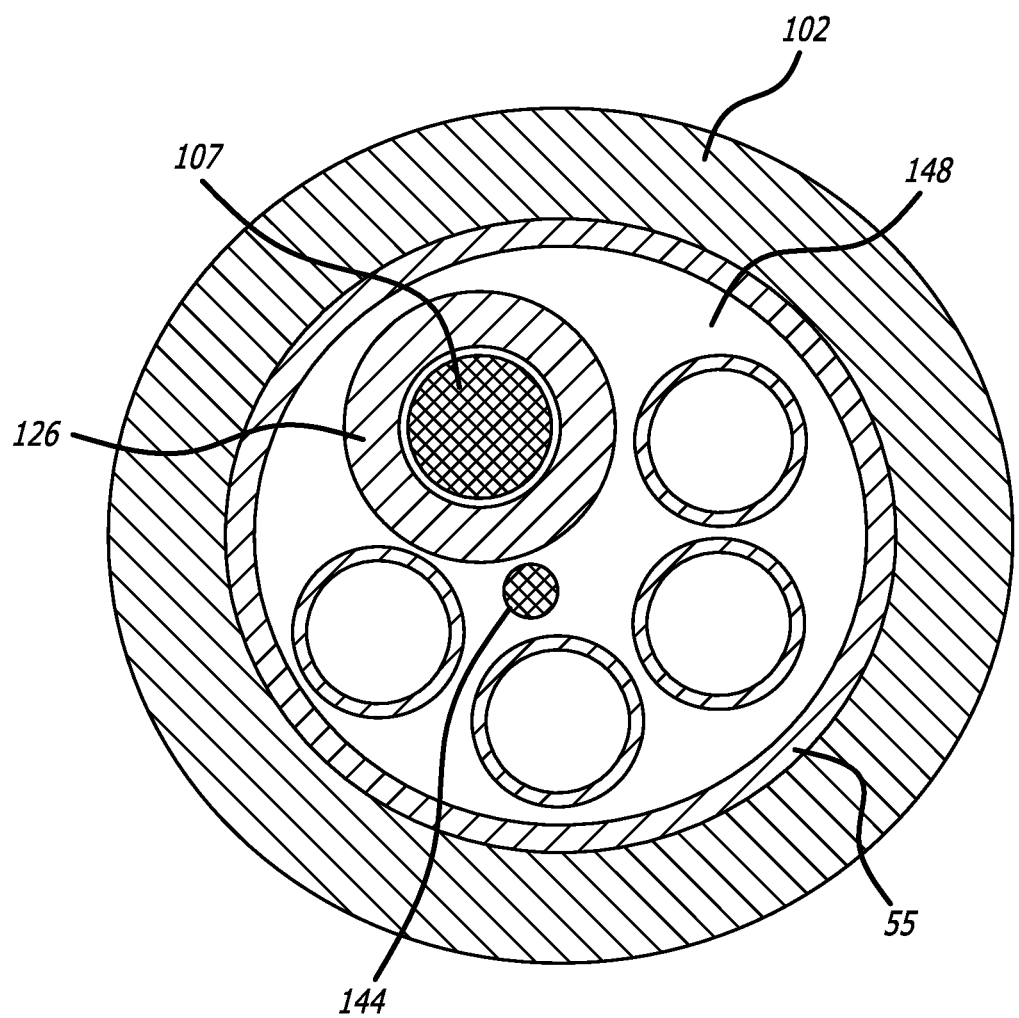
FIG. 13 is a cross-sectional view of the delivery catheter of FIG. 12.

FIG. 13 illustrates a cross-sectional view of the delivery catheter shaft 102 of FIG. 12. In this embodiment, the shaft 102 has a tubular shape with inner lumen 148 and is comprised of a material which provides hoop strength while maintaining flexibility and kink resistance, such as a braided laminated material. Such material may include stainless steel braided or coiled wire embedded in a polymer such as polyurethane, polyester, Pebax, Grilamid TR55, and AESNO to name a few. To provide further support and hoop strength, the tubular member 155 (FIG. 9) is disposed within the lumen 148 of shaft 102 as illustrated in FIG. 13, and the tubular member 55 carries the valve repair assembly 10.

Passing through the lumen 148 are a variety of elongated bodies, including tubular guides and cylindrical rods as required to carry or house various rods or lines for manipulating and deploying the valve repair assembly 10 in the mitral valve. For example, one type of tubular guide is a compression coil 126 extending through lumen 148 from the distal end 122 to the proximal end 124 of the shaft 102, and the actuator rod 107 extends through the compression coil 126. Therefore, the compression coil typically has a length in the range of 48 to 60 in. (121.92 cm to 152.40 cm) and an inner diameter in the range of 0.020 to 0.035 in. (0.5080 mm to 0.8890 mm) to allow passage of the actuator rod 107 therethrough. The actuator rod 107 is manipulable to rotate and translate within and relative to the compression coil 126. The compression coil 126 allows lateral flexibility of the actuator rod 107 and therefore the shaft 102 while resisting buckling and providing column strength under compression. The compression coil may be comprised of 304V stainless steel to provide these properties.

To provide additional tensile strength for the shaft 102 and to minimize elongation, a tension cable 144 may also pass through the support coil 146. The tension cable 144 extends through lumen 148 from the distal end 122 to the proximal end 124 of the shaft 102. Therefore, the tension cable 144 typically has a diameter in the range of 0.005 in. to 0.010 in. (0.1270 mm to 0.2540 mm) and a length in the range of 48 to 60 in. (121.92 cm to 152.40 cm). In preferred embodiments, the tension cable 144 is comprised of 304V stainless steel.

Various other lumens (shafts) are shown in FIG. 13 and can carry rods, lines, or coils to further manipulate and deploy the valve repair assembly 10.

In this embodiment, the elongated bodies (compression coil 126, enclosed actuator rod 107, and tension cable 144 each "float" freely in inner lumen 148 within the tubular member 55 and are fixed only at the distal end 122 and proximal end 124 of shaft 102. The lumen 148 is typically filled and flushed with heparinized saline during use. Alternatively or in addition, the lumen 148 may be filled with one or more fillers, such as flexible rods, beads, extruded sections, gels or other fluids. Preferably the fillers allow for some lateral movement or deflection of the elongated bodies within lumen 148 but in some cases may restrict such movement. Typically, the elongated bodies are fixed at the distal and proximal ends of the shaft and are free to move laterally and rotationally therebetween. Such freedom of movement of the elongated bodies provides the shaft 102 with an increased flexibility as the elongated bodies self-adjust and reposition during bending and/or torquing of the shaft 102. It may be appreciated that the elongated bodies may not be fixed at the distal and proximal ends. The elongated bodies are simply unconstrained relative to the shaft 102 in at least one location so as to be laterally moveable within the lumen 148. Preferably the elongated bodies are unrestrained in at least a proximal portion of the catheter, e.g., 1.969 in. to 5.906 in. (5 cm to 15 cm) from the proximal end 124, so as to provide maximum flexibility in the proximal portion.

While the foregoing is a complete description of the preferred embodiments of the invention, various alternatives, substitutions, additions, modifications, and equivalents are possible without departing from the scope of the invention. For example, in many of the above-described embodiments, the invention is described in the context of approaching a valve structure from the upstream side—that is, the atrial side in the case of a mitral valve. It should be understood that any of the foregoing embodiments may be utilized in other approaches as well, including from the ventricular or downstream side of the valve, as well as using surgical approaches through a wall of the heart. Moreover, the invention may be used in the treatment of a variety of other tissue structures besides heart valves, and will find usefulness in a variety of tissue approximation, attachment, closure, clamping and ligation applications, some endovascular, some endoscopic, and some open surgical.

Again, although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

We claim:

1. A medical device for repairing valve tissue, comprising:
    a proximal member having
        a tubular shape in a compressed configuration, and
        a conical basket shape having a conical taper towards a center point to define an interior portion in an expanded configuration;
    a distal member having
        a tubular shape in a compressed configuration, and
        a conical basket shape having a conical taper towards a center point to define an interior portion in an expanded configuration;
    an elongated shaft extending through the proximal member and to the distal member;
    the distal member being fixed to the elongated shaft and the proximal member initially being separate from the distal member and configured for slidable axial movement along the elongated shaft relative to the distal member; and
    a locking member to lock the proximal member to the distal member after the proximal member is moved along the shaft into contact with the distal member with the valve tissue positioned therebetween;
    wherein one of the proximal member and the distal member is sized to be received within the interior portion defined by the other of the proximal member and the distal member when the proximal member is locked to the distal member.

2. The medical device of claim 1, wherein the proximal member and the distal member are formed from a lattice structure having rigidity in the expanded configuration, and longitudinal flexibility in the compressed configuration.

3. The medical device of claim 1, wherein the proximal member and the distal member have a cross-sectional shape taken from one of a group of cross-sectional shapes including circular, ovoid, elliptical, D-shaped, and non-circular.

4. The medical device of claim 1, wherein the proximal member and the distal member are formed from a metallic material or a polymer material, each that are plastically deformable when expanded from a compressed configuration to an expanded configuration.

5. The medical device of claim 1, wherein the proximal member and the distal member are formed from a lattice structure of interconnected struts having a rectangular cross-section.

6. The medical device of claim 1, wherein the locking member includes a ball mounted to a distal end of the elongated shaft and having a diameter that is greater than a diameter of a proximal portion of the distal member so that as the elongated shaft is moved proximally, the ball pulls a proximal end of the distal member into the distal end of the proximal member thereby locking the proximal member to the distal member with the valve tissue therebetween.

7. The medical device of claim 1, wherein the proximal member has a proximal tubular portion, and wherein a distal diameter of the basket shape having a conical taper is greater than a diameter of the proximal tubular portion.

8. The medical device of claim 1, wherein the proximal member comprises first and second discontinuities in a distal circumference of the proximal member.

9. The medical device of claim 1, wherein the distal member comprises first and second discontinuities in a proximal circumference of the distal member.

10. The medical device of claim 1, wherein the proximal member and the distal member are self-expanding from the compressed configuration to the expanded configuration.

11. The medical device of claim 10, wherein the proximal member and the distal member are formed from a self-expanding shape memory material including at least one of Nitinol, Elgiloy, and a self-expanding polymer.

12. The medical device of claim 1, wherein the proximal member and the distal member in the expanded configuration each has a first diameter at a distal end in the range of 4 mm to 30 mm, and a second diameter at a proximal end in the range of 2 mm to 16 mm.

13. The medical device of claim 12, wherein the first diameter of the distal member is less than the first diameter of the proximal member.

14. The medical device of claim 13, wherein the proximal member and the distal member in the expanded configuration each has a length in the range of 10 mm to 40 mm.

15. The medical device of claim 14, wherein the length of the distal member is less than the length of the proximal member.

16. A medical device for repairing valve tissue, comprising:
    a first basket having
        a tubular shape in a compressed configuration, and
        a conical basket shape having a conical taper towards a center point to define an interior portion in an expanded configuration;
    a second basket having
        a tubular shape in a compressed configuration, and
        a conical basket shape having a conical taper towards a center point to define an interior portion in an expanded configuration;

an elongated shaft extending through the second basket and to the first basket;

the first basket being fixed to the elongated shaft and the second basket initially being separate from the first basket and configured for slidable axial movement along the elongated shaft relative to the first basket; and a locking member to lock the second basket to the first basket after the second basket is moved along the shaft into contact with the first basket with the valve tissue positioned therebetween wherein one of the first basket and the second basket is sized to be received within the interior portion defined by the other of the first basket and the second basket when the second basket is locked to the first basket.

17. The medical device of claim 16, wherein the first basket and the second basket are formed from a lattice structure having rigidity in the expanded configuration, and longitudinal flexibility in the compressed configuration.

18. The medical device of claim 16, wherein the first basket and the second basket have a cross-sectional shape taken from the group of cross-sectional shapes including circular, ovoid, elliptical, D-shaped, and non-circular.

19. The medical device of claim 16, wherein the first basket and the second basket are formed from a metallic material or a polymer material, each that are plastically deformable when expanded from a compressed configuration to an expanded configuration.

20. The medical device of claim 16, wherein the first basket and the second basket are formed from a lattice structure of interconnected struts having a rectangular cross-section.

21. The medical device of claim 16, wherein the locking member includes a ball mounted to a distal end of the elongated shaft and having a diameter that is greater than a diameter of a proximal portion of the first basket so that as the elongated shaft is moved proximally, the ball pulls a proximal end of the first basket into the distal end of the second basket thereby locking the first basket to the second basket with the valve tissue therebetween.

22. The medical device of claim 16, wherein the second basket has a proximal tubular portion, and wherein a distal diameter of the basket shape having a conical taper is greater than a diameter of the proximal tubular portion.

23. The medical device of claim 16, wherein the first basket comprises first and second discontinuities in a proximal circumference of the first basket.

24. The medical device of claim 16, wherein the second basket comprises first and second discontinuities in a distal circumference of the second basket.

25. The medical device of claim 16, wherein the first basket and the second basket are self-expanding from the compressed configuration to the expanded configuration.

26. The medical device of claim 25, wherein the first basket and the second basket are formed from a self-expanding shape memory material including at least one of Nitinol, Elgiloy, and a self-expanding polymer.

27. The medical device of claim 16, wherein the first basket and the second basket in the expanded configuration each has a first diameter at a distal end in the range of 4 mm to 30 mm, and a second diameter at a proximal end in the range of 2 mm to 16 mm.

28. The medical device of claim 27, wherein the first diameter of the second basket is greater than the first diameter of the first basket.

29. The medical device of claim 28, wherein the first basket and the second basket in the expanded configuration each has a length in the range of 10 mm to 40 mm.

30. The medical device of claim 29, wherein the length of the second basket is greater than the length of the first basket.

31. A method for repairing valve tissue, comprising:
providing a medical device including
a proximal member having
a tubular shape in a compressed configuration, and
a conical basket shape having a conical taper towards a center point to define an interior portion in an expanded configuration, and
a distal member having
a tubular shape in a compressed configuration, and
a conical basket shape having a conical taper towards a center point to define an interior portion in an expanded configuration;
positioning the distal member and the proximal member initially separate from each other wherein the proximal member is configured for slidable axial movement along an elongate shaft relative to the distal member to sandwich the valve tissue therebetween with the proximal member and the distal member in the expanded configurations; and
locking the proximal member to the distal member after the proximal member is moved axially into contact with the distal member with the valve tissue positioned therebetween
wherein one of the proximal member and distal member is sized to be received within the interior portion defined by the other of the proximal member and the distal member when the proximal member is locked to the distal member.

32. The method of claim 31, wherein the proximal member and the distal member are self-expanding from the compressed configuration to the expanded configuration.

33. The method of claim 31, wherein a locking member includes a ball mounted to a distal end of an elongated shaft and having a diameter that is greater than a diameter of a proximal portion of the distal member, the method further comprising moving the elongated shaft proximally so that the ball pulls the distal member into the proximal member thereby locking the proximal member to the distal member with the valve tissue therebetween.

* * * * *